US008080382B2

(12) United States Patent
Ahearn et al.

(10) Patent No.: US 8,080,382 B2
(45) Date of Patent: *Dec. 20, 2011

(54) MONITORING IMMUNOLOGIC, HEMATOLOGIC AND INFLAMMATORY DISEASES

(75) Inventors: Joseph M. Ahearn, Sewickley, PA (US); Susan M. Manzi, Wexford, PA (US)

(73) Assignee: University of Pittsburgh - Of the Commonwealth System of Higher Education, Pittsburgh, PA (US)

( * ) Notice: Subject to any disclaimer, the term of this patent is extended or adjusted under 35 U.S.C. 154(b) by 968 days.

This patent is subject to a terminal disclaimer.

(21) Appl. No.: 10/866,509

(22) Filed: Jun. 12, 2004

(65) Prior Publication Data

US 2005/0042602 A1    Feb. 24, 2005

Related U.S. Application Data

(60) Provisional application No. 60/478,493, filed on Jun. 13, 2003.

(51) Int. Cl.
  *G01N 33/53* (2006.01)
(52) U.S. Cl. ........ 435/7.1; 435/7.92; 435/518; 436/811; 436/501
(58) Field of Classification Search .................. None
  See application file for complete search history.

(56) References Cited

U.S. PATENT DOCUMENTS

2005/0037441 A1   2/2005   Ahearn et al.

FOREIGN PATENT DOCUMENTS

| WO | WO 94/10571 A1 | 5/1994 |
| WO | WO 03/022223 A2 | 3/2003 |
| WO | WO 2004/093647 | 11/2004 |

OTHER PUBLICATIONS

Sturfelt, Scan. J. Rheumatol. 2002, vol. 31, p. 129-132.*
Manzi et al. Lupus, 2004, vol. 13, p. 298-303.*
Wolbink et al. J. Immunol. 1996, vol. 157, p. 473-479.*
Bohmig et al. (Journal of American Society of Nephrology, 2001, vol. 12, p. 2482-2489).*
Giles et al. (Clinical Experimental Immunology, 1991, vol. 84, p. 263-269).*
Baldwin et al. (Transplantation 1999, vol. 68, p. 894-900) total of 9 pages of the document generated as a PDF from HTML format.*
Stroncek (Transfusion Medicine, 2003, vol. Feb. 2003, vol. 13, p. 35-41 in IDS of Feb. 20, 2009).*
Freysdottir et al. (Journal of Immunological Methods, 1991, vol. 142, p. 45-52) in IDS Sep. 16, 2005.*
Baldwin et al. (Transplantation 1999, vol. 68, p. 894-900) of record on May 2, 2008.*
Salerno et al.(Xenotransplantation 2002, vol. 9, p. 125-134).*
Iversen et al. (Nephrology Dial Transplant 1993, vol. 8, p. 1211-1214).*
Atkinson, J.P., et al., "*Origin of the Fourth Component of Complement Related Chido and Rodgers Blood Group Antigens*;" 1988; Compliment; vol. 5; pp. 65-76.
Bombardier, Claire, et al., "*Derivation of the SLEDAI A Disease Activity Index for.Lupus Patients*;" Arthritis Rheum, Jun. 1992, vol. 35; No. 6; pp. 630-640.
Buyon, J.P., et al., "*Assessment of disease activity and impending flare in patients with systemic lupus erythematosus*;" Arthritis Rheum, 1992, vol. 35, pp. 1028-1037.
Falk, R.J.., et al., "*Radioimmunoassay of the attack complex of complement in serum from patients with systemic lupus erythematosus*;" N. Engl. J. Med., 1985, vol. 312, pp. 1594-1599.
Jouvin, Marie-Helene et al.; "*Decreased Expression of C3b Receptor (CR1) on Erythrocytes of Patients with Systemic Lupus erythematosus Contrasts with Its Normal Expression in Other Systemic Diseases and Does Not Correlate with the Occurrence or Severity of SLE Nephritis*;" Complement;1986, vol. 3, pp. 88-96.
Lach-Trifilieff, Estelle, et al., "*Complement Receptor 1 (CD35) on Human Reticulocytes: Normal Express in Systemic Lupus Erythematosus and HIV-Infected Patients*;" The Journal Of Immunology, vol. 162, No. 12, Jun. 1999, pp. 7549-7554.
Liang, Matthew H., et al., "*Reliability and Validity of Six Systems for the Clinical Assessment of Disease Activity in Systemic Lupus Erythematosus*," Arthritis Rheum, Sep. 1989, vol. 32; No. 9; pp. 1107-1118.
Manzi, Susan, et al.; "*Measurement of Erythrocyte C4d and Complement Receptor 1 in Systemic Lupus Erythematosus*;" Nov. 2004, Arthritis & Rheumatism, vol. 50, No. 11, pp. 3596-3604.
ACCN. No. 85046338 Medline. McCarthy, T., et al., "*Intrauterine devices and pelvic inflammatory disease*;" Australian and New Zealand Journal of Obstetrics and Gynecology, May 1984, vol. 24, No. 2, pp. 106-110, Abstract.
McGeer, P.L. et al.; "*Reactions of the Immune System in Chronic Degenerative Neurological Diseases*;" The Canadian Journal of Neurological Sciences; 1991, vol. 18; pp. 376-379.
ACCN. No. 90367342 Medline. Meliconi, R., et al., "*Complement activation products in idiopathic pulmonary fibrosis: relevance of fragment Ba to disease severity*;" Clinical Immunology and Immunopathology, Oct. 1990, vol. 57, No. 1, pp. 64-73, Abstract.
Navratil, J.S., et al., "*Apoptosis and autoimmunity: complement deficiency and systemic lupus erythematosus revisited*;" Curr. Rheumatol. Rep., 2000, vol. 2, pp. 32-38.
Ricker, D.M., et al., "*Serum C3 levels are diagnostically more sensitive and specific for systemic lupus erythematosus activity than are serum C4 levels*;" The Lupus Nephritis Collaborative Study Group, Am. J. Kidney Dis., 1991, vol. 18, pp. 678-685.

(Continued)

*Primary Examiner* — Agnieszka Boesen
(74) *Attorney, Agent, or Firm* — Klarkquist Sparkman, LLP

(57) ABSTRACT

This invention relates to the diagnosis and/or monitoring of patients with inflammatory diseases or conditions, e.g., immunologic, hematologic, vascular, or infectious diseases or conditions, by determining levels of complement pathway components on erythrocytes. Methods of diagnosing vascular diseases or conditions by determining levels of complement pathway components on platelets are also disclosed.

16 Claims, 6 Drawing Sheets

OTHER PUBLICATIONS

Senaldi, G., et al., "*Correlation of the activation of the fourth component of complement (C4) with disease activity in systemic lupus erythematosus;*" Ann. Rheum. Dis., 1988, vol. 47, pp. 913-917.

Tausk, Francisco, et al., "*The Expression of C3b Receptors in the Differentiation of Discoid Lupus Erythematosus and Systemic Lupus Erythematosus;*" Arthritis and Rheumatism, Jun. 1990, vol. 33, No. 6, pp. 888-892.

Tilley, C.A., et al., "*Localisation of Chido and Rodgers Determinants to the C4d Fragment of Human C4;*" Nature; Dec. 14, 1978; vol. 276; pp. 713-715.

Tsuboi, Y. et al.; "*Increased concentration of C4d complement protein in CSF in amyotrophic lateral sclerosis*"; Neurosurgery and Psychiatry 1994, vol. 57, pp. 859-861.

Yamada, T., et al. "*Complement-activated oligodendroglia: a new pathogenic entity identified by immunostaining with antibodies to human complement proteins C3d and C4d;*" Neuroscience Letters, 1990, vol. 112, pp. 161-166.

Alexander, EL., et al., "Serum complement activation in central nervous system disease in sjogren's syndrome," *The American Journal of Medicine*, Oct. 1988, vol. 85, No. 4, abstract only.

Chudwin, D., et al., "Activation of the Alternative Complement Pathway by Red Blood Cells from Patients with Sickle Cell Disease," *Clinical Immunology and Immunopathology*, May 1994, vol. 71, No. 2, pp. 199-202.

Corvetta, Angelo et al.; "Low Number of Complement C3b/C4b Receptors (CR1) on Erythrocytes from Patients with Essential Mixed Cryoglobulinemia, Systemic Lupas Erythematosus and Rheumatoid Arthritis: Relationship with Disease Activity, Anticardiolipin Antibodies, Complement Activation and Therapy"; 1981, *J. Rheumatol.*, vol. 18, pp. 1021-1025.

Cosio, F.G., et al., "The high prevalence of severe early posttransplant renal allograft pathology in hepatitis C positive recipients," *Transplantation*, Oct. 27, 1996, vol. 62, No. 8, abstract only.

Freysdottir, Jona et al.; "A flow cytometric assay for measuring complement receptor 1 (CR1) and the complement fragments C3d and C4d on erythrocytes"; 1991, *Journal of Immunological Methods*, vol. 142, pp. 45-52.

Lamprecht, P., et al., "Immunological and clinical follow up of hepatitis C virus associated cryoglobulinaemic vasculitis," *Annals of the Rheumatic Diseases*, Apr. 2001, vol. 60, pp. 385-390.

Manzi, Susan et al.; "Sensitivity and Specificity of Plasma and Urine Complement Split Products as Indicators of Lupus Disease Activity"; 1996, *Arthritis & Rheumatism*, vol. 39, No. 7, pp. 1178-1188.

Manzi, Susan et al.; "New insights into complement: a mediator of injury and marker of disease activity in systemic lupus erythematosus"; 2004, *Lupus*, vol. 13, pp. 1-6.

Ross, Gordon D. et al.; "Disease-Associated Loss of Erythrocyte Complement Receptors ($CR_1$, C3b Receptors) in Patients with Systemic Lupus Erythematosus and other Diseases Involving Autoantibodies and/or Complement Activation"; 1985, *Journal of Immunology*, vol. 135, No. 3, pp. 2005-2014.

Sirois, M., et al., "An Enzyme-linked Immunosorbent Assay for the Detection of Complement Components on Red Blood Cells," *Am. Journ. Clin. Path.*, Jul. 1984, vol. 82, No. 1, pp. 67-73.

Chaplin H. Jr. et al: "Characterization of Red Blood Cells Strongly Coated In Vitro by C3 via the Alternative Pathway" Transfusion (Bethesda), vol. 20, No. 3, 1980, pp. 256-262.

Hong F. et al: "Complement activation by artificial blood substitute Fluosol: in vitro and in vivo studies" Transfusion (Bethesda), vol. 31, No. 7, 1991, pp. 642-647.

Kanto T. et al: "Low expression of erythrocyte complement receptor type 1 induces defective immune complex clearance in chronic hepatitis C patients" Hepatology, vol. 22, No. 4. Part 2, 1995, p. 339a, & 46th Annual Meeting and Postgraduate Course of the American Association for the Study of Liver Disease; Chicago, Illinois, USA, Nov. 3-7, 1995.

Kanto Tatsuya et al: "Low expression of Erythrocyte Complement Receptor Type 1 in Chronic Hepatitis C Patients" Journal of Medical Virology, vol. 50, No. 2, 1996, pp. 126-134.

Mauiyyedi Shamila et al: "Acute Humoral Rejection in Kidney Transplantation: II. Morphology, Immunopathology, and Pathologic Classification" Journal of the American Society of Nephrology: JASN Mar. 2002, vol. 13, No. 3, Mar. 2002, pp. 779-787.

Meliconi R. et al: "Complement Activation Products in Idiopathic Pulmonary Fibrosis: Relevance of Fragment Ba to Disease Severity" Clinical Immunology and Immunopathology, vol. 57, No. 1, 1990, pp. 64-73.

Miyaike J. et al: "Regulation of circulating immune complexes by complement receptor type 1 on erythrocytes in chronic viral liver diseases" GUT, vol. 51, No. 4, Oct. 2002, pp. 591-596.

Rascusen L.C. et al: "Antibody-Mediated Rejection Criteria—an Addition to the Banff '97 Classification of Renal Allograft Rejection" American Journal of Transplantation 2003 Denmark, vol. 3, No. 6, May 28, 2003, pp. 708-714.

Regele Heinz et al: "Capillary Deposition of Complement Split Product C4d in Renal Allografts is Associated with Basement Membrane Injury in Peritubular and Glomerular Capillaries: A contribution of Humoral Immunity to Chronic Allograft Rejection" Journal of the American Society of Nephrology, vol. 13, No. 9, Sep. 2002, pp. 2371-2380.

Segerer, Stephan et al: "When Renal Allografts Turn DARC" Transplantation Apr. 15, 2003, vol. 75, No. 7, pp. 1030-1034.

Solling J: "Circulating Immune Complexes and Complement Breakdown Product C3d in Glomerulonephritis and Kidney Transplantation" Acta Pathologica Microbiologica ET Immunologica Scandinavica Section C Immunology, vol. 92, No. 4, 1984, pp. 213-220.

Sung K.-L. P. et al: "Effect of complement on the viscoelastic properties of human erthrocyte membrane" British Journal of Haematology, vol. 61, No. 3, 1985, pp. 455-466.

D. F. Stroncek et al., "A preliminary comparison of flow cytometry and tube agglutination assays in detecting red blood cell-associated C3d", Transfusion Medicine, 2003, pp. 35-41, vol. 13.

Abe et al., "Pertubular Capillary Deposition of C4d Fragment in Allograft Rejection After Renal Transplantation," $39^{th}$ Complement Symposium, $13^{th}$ Meeting of Japanese Society for Bio-Defense Research, p. 50 (2002) (in Japanese, with English language translation).

Adinolfi et al., "Ontogeny of Human Complement Receptors cr1 and cr3: Expression of these Molecules on Monocytes and Neutrophils from Maternal, Newborn and Fetal Samples," *Eur. J. Immunol.* 18:565-569 (1988).

Ishii et al., "Cold Activation of Serum Complement in Paitents with Chronic Hepatitis C: Study on Activating Pathway and Involvement of IgG," *Acta Med. Okayama* 55(4):229-235 (2001).

Mold et al., "Complement Activation During Painful Crisis in Sickle Cell Anemia," *Clinical Immunology and Immunology* 76(3):314-320 (Sep. 1995).

Kohsaka et al., "Classical Pathway Complement Activation in Kawasaki Syndrome," *Journal of Allergy and Clinical Immunology* 93(2): 520-525 (Feb. 2004).

Shirey et al., "Fenoprofen-Induced Immune Hemolysis, Difficulties in Diagnosis and Complication in Compatibility Testing," *American Journal of Clinical Pathology* 89(3):410-414 (1988).

Yasuda et al., "The Complement System in Ischemic Heart Disease," *Circulation* 81(1):156-163 (Jan. 1990).

\* cited by examiner

MONITORING IMMUNOLOGIC, HEMATOLOGIC AND INFLAMMATORY DISEASES

CROSS-REFERENCES TO RELATED APPLICATIONS

This application claims the benefit of U.S. Provisional Application No. 60/478,493, filed Jun. 13, 2003, which is herein incorporated by reference for all purposes.

FIELD OF THE INVENTION

This invention relates to the diagnosis and/or monitoring of patients with inflammatory diseases or conditions, e.g., immunologic, hematologic, vascular, or infectious diseases or conditions, by determining levels of complement pathway components on erythrocytes. Methods of diagnosing vascular diseases or conditions by determining levels of complement pathway components on platelets are also disclosed.

BACKGROUND OF THE INVENTION

This invention relates to the diagnosis and/or monitoring of patients with immunologic, hematologic, and inflammatory conditions and diseases. Measurement of complement ligand C4d and its receptor CR1 on surfaces of erythrocytes provides a highly sensitive and specific test for diagnosis and measurement of disease activity in patients with systemic lupus erythematosus (SLE) or scleroderma. See, e.g., PCT/US02/28910, which is herein incorporated by reference for all purposes. Patterns of complement ligand and receptor expression that facilitate diagnosis and disease activity monitoring in other human immunologic, hematologic, and inflammatory conditions and diseases have not been identified. The present invention addresses this and other needs.

BRIEF SUMMARY OF THE INVENTION

The present invention provides a method for diagnosing or monitoring an inflammatory disease or condition in an individual, with the caveat that the inflammatory disease or condition is not systemic lupus erythematosus or scleroderma. The method involves, (a) determining, in a blood sample from the individual containing erythrocytes, a level of a complement pathway component on surface of an erythrocyte in the sample, and (b) comparing the complement pathway component level with a control level of complement pathway component, where a difference from the control level of the complement pathway component indicates that the individual has the inflammatory disease or condition. As an example, the inflammatory disease or condition can be selected from hepatitis C infection or a complication of the disease, such as cryoglobulinemia; sickle cell anemia, or a complication of the disease, such as a vasoocclusive crisis; a complication of a transplantation procedure; and a complication of pregnancy.

In one embodiment, the inflammatory disease or condition is a hepatitis C infection or a complication of the disease, such as cryoglobulinemia. Exemplary complement pathway components useful to diagnose or monitor a hepatitis C infection or a complication of the disease include complement ligand Bb and complement pathway component C3d. Bb and C3d levels can be determined individually or together to make the diagnosis. Antibodies specific for complement component Bb or complement component C3d can be used to determine their levels. The antibodies can be labeled and polyclonal or monoclonal antibodies can be used. Levels of additional complement pathway components can be determined.

In one embodiment, the inflammatory disease or condition is sickle cell anemia or a complication of the disease, such as a vasooclusive crisis. Exemplary complement pathway components useful to diagnose or monitor a sickle cell or a complication of the disease include complement ligand C4d. Antibodies specific for complement component C4d can be used to determine its level. The antibodies can be labeled and polyclonal or monoclonal antibodies can be used. Levels of additional complement pathway components can be determined, as well.

In one embodiment, the inflammatory disease or condition is a complication of a transplant procedure. Exemplary complement pathway components useful to diagnose or monitor a complication of a transplant procedure include complement pathway component C4d, complement pathway component C3d, and complement pathway component iC3b. C4d, C3d, and iC3b levels can be determined individually or together to make the diagnosis. Antibodies specific for C4d, C3d, and iC3b can be used to determine their levels. The antibodies can be labeled and polyclonal or monoclonal antibodies can be used. Levels of additional complement pathway components can be determined.

In one embodiment, the inflammatory disease or condition is a complication of pregnancy, such as preeclampsia. Exemplary complement pathway components useful to diagnose or monitor a complication of a pregnancy include complement pathway component C4d and complement pathway component CR1. C4d and CR1 levels can be determined individually or together to make the diagnosis. Antibodies specific for C4d and CR1 can be used to determine their levels. The antibodies can be labeled and polyclonal or monoclonal antibodies can be used. Levels of additional complement pathway components can be determined.

The present invention also provides a kit for diagnosing or monitoring an inflammatory disease or condition in an individual, with the caveat that the inflammatory disease or condition is not systemic lupus erythematosus or scleroderma. The kit includes an antibody specific for a complement pathway component and a means for comparing a level of the complement pathway component to a control level of complement pathway component.

The present invention also provides a computer readable medium, comprising (a) code for receiving data corresponding to a determination of a complement pathway component deposited on surfaces of erythrocytes (b) code for retrieving a reference value for the complement pathway component deposited on surfaces of erythrocytes of individuals; (c) code for comparing the data in (a) with the reference value in (b), wherein the comparison of data is used to diagnose or monitor an inflammatory disease or condition in an individual, with the caveat that the inflammatory disease or condition is not systemic lupus erythematosus or scleroderma.

In another aspect, the invention provides method for diagnosing or monitoring a vascular disease or condition in an individual, by (a) determining, in a blood sample from the individual containing platelets, a level of a complement pathway component on surface of an platelet in the sample, and (b) comparing the level to a control level of the complement pathway component, where a difference from the control level of the complement pathway component indicates that the individual has the vascular disease or condition. In some embodiments, the complement pathway component is selected from C1, C4, C2, C3 and fragments thereof, e.g., C1q, C1r, C1s, C4a, C4b, C2a, C2b, C4bC2a, C3a, C3b, C4c, C4d, iC3b, iC4b, C3d, C3i, C3d g. Also included are C5, C5b, C6, C7, C8, C9, C1inh, MASP1, MASP2, MBL, MAC, CR1, DAF, MCP, C4 binding protein (C4BP), protein factor H, Factor B, C3bB, Factor D, Bb, Ba, C3bBb, properdin, C3bBb, CD59, C3aR, C5aR, C1qR, CR2, CR3, and CR4. The diagnosis of vascular disease can be made in normal individuals and in individuals who have already been diagnosed with SLE.

DETAILED DESCRIPTION OF THE INVENTION

Introduction

Figure 1:
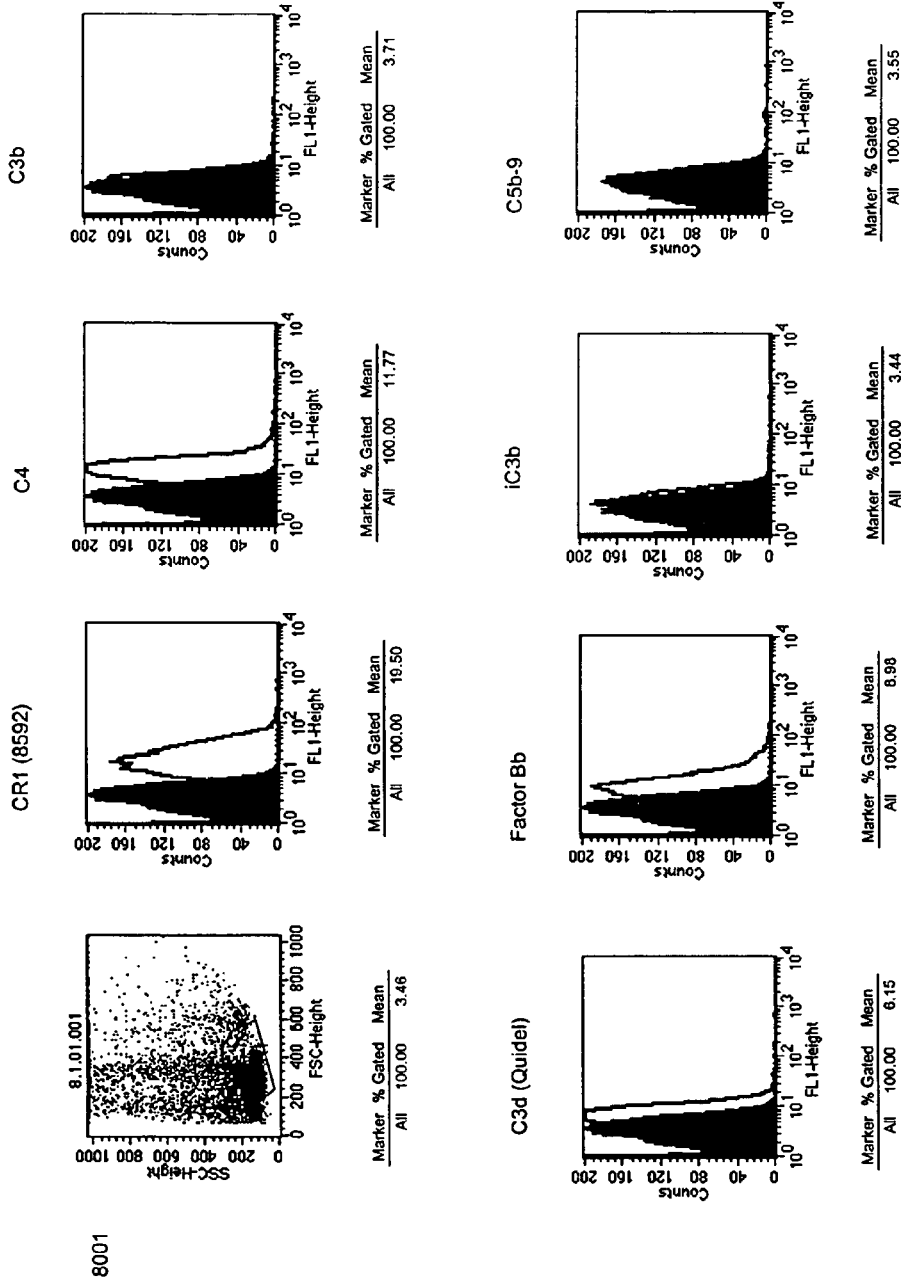
FIG. 1 provides a complement pathway component profile of erythrocytes from an individual infected with hepatitis C virus (HCV).

This disclosure teaches diagnosis, monitoring, or prediction of inflammatory diseases or conditions by determining a level of a complement pathway component in a sample from an individual and comparing it to a control level of the complement pathway component. While the inflammatory disease SLE is characterized by decreased E-CR1 and increased E-C4d, other inflammatory conditions and diseases can also be characterized by patterns of complement ligand and receptor expression on erythrocytes or other blood products, such as platelets. Such patterns can include one or more of the complement receptors including but not limited to CR1, and ligands generated through activation of the classical (C1, C4, C2), alternative (B, D, P, C3), or terminal (C5, C6, C7, C8, C9) pathways of complement activation. Levels of complement ligand and receptor can be differentially increased or decreased. Patterns can be diagnostic and static or they can be dynamic and used as biomarkers or surrogate markers in monitoring disease activity. These measurements can also be used in efforts to identify subsets of patients with the same general diagnosis and to predict disease course, or response to therapy for individual patients.

Another use of this invention is to monitor complement activation during the course of human diseases. Current state-of-the-art methods rely on measurement of serum or plasma levels of soluble complement C3 and/or C4. However there are known inadequacies with this approach. For example, C3 and C4 are parent molecules and they are precursors to activation of the complement cascade. Increased hepatic and extra-hepatic synthesis of C3 and C4 can balance increased C3 and C4 catabolism during activation of the complement cascade resulting in misleading change or lack or change in serum levels. In addition, genetic deficiencies of C4 are well documented and result in abnormally low serum/plasma levels of C4 due to lack of synthetic capacity that can be misinterpreted as being due to increased C4 consumption during complement activation. The invention described herein is based upon measurement of protein products of complement activation such as C3d, C4d, and others that are attached to surfaces of circulating blood cells such as erythrocytes, platelets, lymphocytes, reticulocytes, and others. This enables monitoring levels of activation products as opposed to reactants, and eliminates the weaknesses inherent in measuring C3 and C4 described above.

Definitions

As used herein, an "inflammatory disease or condition" refers to any disease or condition that causes increased inflammation in an individual, e.g., immune system disorders, infectious diseases, or cancer. In some embodiments the inflammatory disease or condition is a "chronic inflammatory disease or condition." A chronic inflammatory disease or condition is an inflammatory condition that does not resolve after a period of weeks, months or longer. Chronic inflammatory conditions can follow an acute inflammatory condition, or for some diseases or conditions can occur in the absence of an acute inflammatory disease or condition. An inflammatory disease or condition includes the following: autoimmune system diseases, including systemic lupus erythematosus (lupus or SLE), rheumatoid arthritis, vasculitis (and its specific forms such as Wegener's granulomatosis), scleroderma, myositis, serum sickness, transplant rejection, graft versus host disease, sickle cell anemia, gout, complications of pregnancy such as pre-eclampsia, multiple sclerosis, cardiovascular disease, infectious diseases such as hepatitis virus infection, including hepatitis A, B, C, and D, HIV infection, West Nile virus, Lyme disease, etc. Each of these diseases or conditions can also be described as chronic inflammatory diseases or conditions.

Inflammatory disease or condition also refers to cancer, e.g., solid tumors and hematological malignancies. The former includes cancers such as breast, colon, and ovarian cancers. The latter include hematopoietic malignancies including leukemias, lymphomas and myelomas.

Leukemias are generally neoplastic disorders of hematopoietic stem cells, and include adult and pediatric acute myeloid leukemias (AML), chronic myeloid leukemia (CML), acute lymphocytic leukemia (ALL), chronic lymphocytic leukemia (CLL), hairy cell leukemia and secondary leukemia. Specific leukemias include acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

Lymphomas are generally neoplastic transformations of cells that reside primarily in lymphoid tissue. Among lymphomas, there are two major distinct groups: non-Hodgkin's lymphoma (NHL) and Hodgkin's disease. Lymphomas are tumors of the immune system and generally are present as both T cell- and as B cell-associated disease. Other hematological malignancies include myelodysplastic syndromes (MDS), myeloproliferative syndromes (WS) and myelomas, such as solitary myeloma and multiple myeloma. Multiple myeloma (also called plasma cell myeloma) involves the skeletal system and is characterized by multiple tumorous masses of neoplastic plasma cells scattered throughout that system. It may also spread to lymph nodes and other sites such as the skin. Solitary myeloma involves solitary lesions that tend to occur in the same locations as multiple myeloma.

Other cancers are also of concern, and include those characterized by solid tumors. Examples of other cancers of concern are skin cancers, including melanomas, basal cell carcinomas, and squamous cell carcinomas. Epithelial carcinomas of the head and neck are also encompassed by the present invention. The present invention also encompasses cancers of the lung. Lung cancers include squamous or epidermoid carcinoma, small cell carcinoma, adenocarcinoma, and large cell carcinoma. Breast cancer is also included, both invasive breast cancer and non-invasive breast cancer, e.g., ductal carcinoma in situ and lobular neoplasia. The present invention also encompasses gastrointestinal tract cancers. Gastrointestinal tract cancers include esophageal cancers, gastric adenocarcinoma, primary gastric lymphoma, colorectal cancer, small bowel tumors and cancers of the anus. Pancreatic cancer and cancers that affect the liver are also of concern, including hepatocellular cancer. The present invention also includes treatment of bladder cancer and renal cell carcinoma.

The present invention also encompasses prostatic carcinoma and testicular cancer.

Gynecologic malignancies are also encompassed by the present invention including ovarian cancer, carcinoma of the fallopian tube, uterine cancer, and cervical cancer.

Treatment of sarcomas of the bone and soft tissue are encompassed by the present invention. Bone sarcomas include osteosarcoma, chondrosarcoma, and Ewing's sarcoma.

The present invention also encompasses malignant tumors of the thyroid, including papillary, follicular, and anaplastic carcinomas.

As used herein, "systemic lupus erythematosus", "SLE", or "lupus" is the prototypic autoimmune disease resulting in multiorgan involvement. This anti-self response is characterized by autoantibodies directed against a variety of nuclear and cytoplasmic cellular components. These autoantibodies bind to their respective antigens, forming immune complexes which circulate and eventually deposit in tissues. This immune complex deposition and consequential activation of the complement system causes chronic inflammation and tissue damage.

SLE progresses in a series of flares, or periods of acute illness, followed by remissions. The symptoms of a flare, which vary considerably between patients and even within the same patient, include malaise, fever, symmetric joint pain, and photosensitivity (development of rashes after brief sun exposure). Other symptoms of SLE include hair loss, ulcers of mucous membranes and inflammation of the lining of the heart and lungs which leads to chest pain. Red blood cells, platelets and white blood cells can be targeted in lupus, resulting in anemia and bleeding problems. More seriously, immune complex deposition and chronic inflammation in the blood vessels can lead to kidney involvement and occasionally failure requiring dialysis or kidney transplantation. Since the blood vessel is a major target of the autoimmune response in SLE, premature strokes and heart disease are not uncommon. Over time, however, these flares can lead to irreversible organ damage.

As used herein, "systemic sclerosis or scleroderma" is a chronic disorder of connective tissue characterized by inflammation and fibrosis and by degenerative changes of the blood vessels, skin, gastrointestinal tract, lung, heart and kidney. Sclerodermna is a disabling and life-threatening disease. Criteria have been developed for the classification of patients with scleroderma (Masi, et al. *Arth Rheum;* 23:581-590 (1980)). These criteria are intended for description of large series of patients in research studies and not for diagnosis of individual patients. The major criterion is sclerodermatosus skin changes (thickening of the skin) in any location proximal to the digits. With the addition of any two or three minor criteria [sclerodactyly (skin thickening involving the digits), digital pitting scars, bibasilar pulmonary interstitial fibrosis] the sensitivity for the diagnosis increases. However, nearly 10% of individuals with definite scleroderma do not satisfy these criteria (Medsger T A Jr. Comment on scleroderma criteria cooperative study. In: Black C M, Myers A R, eds. Current Topics in Rheumatology: Systemic Sclerosis. New York: Gower Medical Publishing, 1985:16-17).

The status of a scleroderma patient or "severity" of his/her disease at a given time represents some combination of irreversible changes or "damage" and potentially reversible changes or "activity." Inflammation, early in the course of disease, leads to fibrosis and scarring later. If one could accurately detect the inflammatory activity, early intervention may prevent future irreversible damage. However, it is often difficult for clinicians to distinguish disease damage from disease activity. In part, this may be because clinical evidence of activity can be extremely subtle. In addition, there is no reliable laboratory marker of inflammation. Cross-sectional and longitudinal assessment of disease damage and activity are essential in evaluating the natural history of disease and in measuring the effectiveness of interventions, both in individual patients and in clinical trials. A review of this disorder can be found in Medsger T A Jr. Systemic sclerosis (scleroderma): clinical aspects. In: Koopman W J, ed. Arthritis and Allied Conditions. 13th ed. Philadelphia: Lea and Febiger, 1997: 1433-1464.

As used herein, an "erythrocyte" refers to a mature red blood cell. Erythrocytes are usually obtained by taking a blood sample from an individual. In some embodiments, an erythrocyte is isolated from a blood sample of an individual before determining the level of a complement component on the erythrocyte.

As used herein, the "complement pathway or system" refers to a complex network of more than 30 functionally linked proteins that interact in a highly regulated manner to provide many of the effector functions of humoral immunity and inflammation, thereby serving as the major defense mechanism against bacterial and fungal infections. This system of proteins acts against invasion by foreign organisms via three distinct pathways: the classical pathway (in the presence of antibody) or the alternative pathway (in the absence of antibody) and the lectin pathway. Once activated, the proteins within each pathway form a cascade involving sequential self-assembly into multimolecular complexes that perform various functions intended to eradicate the foreign antigens that initiated the response. For a review of the complement pathway, see, e.g., Sim and Tsiftsoglou, *Biochem. Soc. Trans.* 32:21-27 (2004).

The classical pathway is usually triggered by an antibody bound to a foreign particle. It consists of several components that are specific to the classical pathway and designated C1, C4, C2. Sequentially, binding of C1q to an antigen-antibody complex results in activation of C1r and C1s (both are serine proteases), and activated C1s cleaves C4 and C2 into, respectively, C4a and C4b and C2a and C2b. Fragments C4b and C2a assemble to form C4b2a, which cleaves protein C3 into C3a and C3b, which completes activation of the classical pathway. Fragments C4b and C3b are subject to further degradation by Factor I. This factor cleaves C4b to generate C4d and also cleaves C3b, to generate iC3b followed by C3d. Thus, activation of the classical pathway of complement can lead to deposition of a number of fragments, such as C4d, iC3b, and C3d, on immune complexes or other target surfaces. Such targets include cells circulating in the blood, e.g., lymphocytes and other white blood cells, erythrocytes and platelets.

Activation of the alternative complement pathway begins when C3b (or C3i) binds to e.g., the cell wall or other surface components of a microbe. Alternative pathway protein Factor B then combines with the cell-bound C3b to form C3bB. Factor D then splits the bound Factor B into Bb and Ba, forming C3bBb. A serum protein called properdin then binds to the Bb to form C3bBbP, which functions as a C3 convertase that lyses C3 into C3a and C3b.

The lectin complement pathway is mediated by mannan-binding lectin or mannan-binding protein (MBP). MBP is a protein that binds to the mannose groups found in many microbial carbohydrates. The MBP appears to be functionally equivalent to C1q in the classical complement pathway. Activation of the lectin pathway begins when MBP binds to the mannose groups of microbial carbohydrates. Two more lectin pathway proteins called MASP1 and MASP2 (functionally equivalent to C1r and C1s of the classical pathway) then bind to the MBP. The MASP1/MASP2/MBL complex forms an enzyme with activity similar to C1 of the classical complement pathway that is able to cleave C4 and C2 to form C4b C2a, a C3 convertase that lyses C3 into C3a and C3b. The C3 convertase cleaves and activates complement pathway components to form a membrane attack complex (MAC) that forms a pore in a bacterial cell wall, lysing the bacterial cell.

As used herein a "complement pathway component" includes proteins from the classical, alternative, and lectin complement pathways, e.g., C1, C4, C2, C3 and fragments thereof, e.g., C1q, C1r, C1s, C4a, C4b, C2a, C2b, C4b C2a, C3a, C3b, C4c, C4d, iC3b, iC4b, C3d, C3i, C3dg. Also included are C5, C5b, C6, C7, C8, C9, C1inh, MASP1, MASP2, MBL, MAC, CR1, DAF, MCP, C4 binding protein (C4BP), protein factor H, Factor B, C3bB, Factor D, Bb, Ba, C3bBb, properdin, C3bBb, CD59, C3aR, C5aR, C1qR, CR2, CR3, and CR4, as well as other complement pathway components, receptors and ligands not listed specifically herein.

As used herein, a "control level of the complement pathway component" refers, in some embodiments, to a level of a complement pathway component on a cell from an individual who does not suffer from a chronic inflammatory disease or condition. A control level can also be determined by analysis of a population of individuals. In some embodiments, the control level of a complement pathway component is from the same individual for whom a diagnosis is sought or whose disease is being monitored, but is obtained at a different time. A control level of a complement pathway component can also be used as a reference value for a complement pathway component in a computer readable medium.

As used herein, "a difference from a control level" refers to a statistically significant difference between a control level of a complement pathway component and a level of a complement pathway component from an individual for whom diagnosis or other information is sought, i.e., an experimental level. Those of skill will recognize that many methods are available to determine whether a difference is statistically significant and the particular method used is not limiting to the invention.

As used herein, the term "hepatitis" relates generally to a disease or condition characterized by an inflammation of the liver. The term "hepatitis C" relates more specifically to an infection by the hepatitis C virus (HCV). The introduction of the hepatitis C virus into a host is usually by parenteral means and typically marked by blood to blood contact. In many instances, the infection by HCV is chronic, and can lead to severe liver dysfunction and death. The symptoms of hepatitis C virus infection include, but are not limited to: abdominal pain, loss of appetite, liver cirrhosis, autoimmune complications, liver cancer, cryoglobulinemia, anxiety, arthritis, ascites (swelling in the stomach area), blurred vision, chills, dark urine, decline in sex drive, depression, dizziness, dry skin, edema (swelling of the hands, feet & legs), excessive bleeding, excessive gas, eye or eyesight problems (blurred vision or dry eyes), fatigue, fever, flu like symptoms, gallstones, grey, yellow, white or light colored stools, headaches, hepatalgia (pain or discomfort in liver area), hot flashes, indigestion, inflammation in the joints, insomnia, irritability, itching, jaundice (yellowing of eyes and/or skin), joint pain, kidney disease, lichen planus (a skin disease), mood changes or swings, memory loss, mental confusion, menstrual problems, muscle aches, nausea, neuropathy, rashes/red spots, red palms, rheumatoid symptoms, sensitivity to heat or cold, sleep disturbances, slow healing and recovery, sensitivity to sunlight (porphyria cutanea tarda), sialadenitis (inflammation of the salivary glands), susceptibility to illness/flu, sweating, vertigo, vomiting, water retention, weakness, weight gain, weight loss.

As used herein, "autoimmune complications" of HCV infection relate to activation of an autoimmune response in a patient. This response generally is directed at the liver, causing fatigue, low-grade fever and jaundice, but may also involve extrahepatic tissues, causing, among other symptoms: amenorrhea (absence of menstrual period), bloody diarrhea (due to ulcerative colitis), abdominal pain, arthritis, rashes, anemia, glomerulonephritis (a form of kidney disease), dry eyes, keratoconjunctivitis sicca, Mooren's ulcer and dry mouth.

As used herein, "cryoglobulinemia", refers generally to the condition of having the immunoglobulin, cryoglobulin, in the blood. At cool temperatures, these cryoglobulins turn into a gel, and may cause inflammation of the blood vessels. Deposition of circulating immune complexes and complement in cryoglobulinemia can result in systemic vasculitis.

As used herein, "specific therapy" for hepatitis C infection includes, but is not limited to, the administration of antiviral medications, including interferon, ribavirin and PEG-interferon.

As used herein, "sickle cell anemia" refers to an inherited disease caused by an abnormality in a hemoglobin protein, e.g., hemoglobin S (sickle hemoglobin), HbC, HbD, and HbO-Arab. The term sickle cell anemia also includes diseases such as sickle cell-$b^0$ thalassemia, hemoglobin SC disease, or sickle cell-$b^+$ thalassemia. Sickle cell anemia can be diagnosed by sequencing the DNA of a patient for the underlying mutation. Red blood cells in sickle cell anemia become disc shaped, fragile and inflexible, leading to a variety of symptoms of the disease, e.g., joint pain and other bone pain, fatigue, breathlessness, rapid heart rate, delayed growth and puberty, susceptibility to infections, ulcers on the lower legs (in adolescents and adults), jaundice, bone pain, attacks of abdominal pain, and fever.

Sickle cell anemia can become life-threatening when damaged red blood cells break down (hemolytic crisis), when the spleen enlarges and traps the blood cells (splenic sequestration crisis), or when a certain type of infection causes the bone marrow to stop producing red blood cells (aplastic crisis). Repeated crises can cause damage to the kidneys, lungs, bones, eyes, and central nervous system. Blocked blood vessels and damaged organs can also cause acute painful episodes. These painful crises, which occur in almost all patients at some point in their lives, can last hours to days, affecting the bones of the back, the long bones, and the chest.

As used herein, "transplantation procedure" refers to transfer of an organ, e.g., heart, lungs, kidney, cornea, or liver, or of cells from a donor to a recipient. In preferred embodiments, the donor is a human and the recipient is a human. In some embodiments, the transplantation procedure is a bone marrow transplant, in which healthy bone marrow is transferred from a donor to a recipient who lacks functioning bone marrow or has a disease associated with blood cells, such as leukemia.

A "complication of a transplantation procedure" includes transplant rejection, graft versus host disease (GVDH), and infection. Identification of changes in complement pathway components on erythrocytes that are associated with complications of transplant procedures can lead to more effective and targeted therapeutic intervention or be used to predict the outcome of the transplantation procedure.

As used herein, the term "pregnancy" relates generally to the state of containing unborn young within the body. Normally, pregnancy progresses smoothly from conception to birth. However, pregnancy may include complications which include, but are not limited to, one or more of the following: fetal birth defects, ectopic pregnancy, bleeding, miscarriage, loss of amniotic fluid, gestational diabetes, toxoplasmosis, group B strep association, RH disease, obstetric cholestatis, high blood pressure, uterine prolapse, morning sickness, pregnancy induced hypertension, placenta previa, fetal distress, blighted ovum, hyperemesis gravidarum, dystocia, fibroids and preeclampsia. The term, "preeclampsia" or "toxemia" or "pregnancy-induced hypertension", as used herein, refers to the development of swelling, elevated blood pressure, and protein in the urine during pregnancy. Symptoms of preeclampsia include, but are not limited to: edema, weight gain in excess of two pounds per week, headache, decreased urine output, nausea, vomiting, facial swelling, high blood pressure, agitation, vision changes and abdominal pain. Preeclampsia has been associated with certain autoimmune disorders including systemic lupus erythematosus (also known as "lupus" or "SLE") and anti-phospholipid syndrome (also known as "antiphospholipid syndrome" or "APS"). As used herein, the term "anti-phospholipid syndrome" or "antiphospholipid syndrome" or "APS" refers to an autoimmune disease where the body recognizes phospholipids as foreign and produces antibodies against them. APS is often associated with fetal loss during pregnancy with antiphospholipid antibodies present in about one in five women with recurrent pregnancy losses. The causes of this are unknown, but may be due to the creation of blood clots in the mother.

The causes of complications during pregnancy are often difficult to diagnose, especially those associated with autoimmune disorders, such as lupus and APS, as they often show similar symptoms. Further, complications associated with lupus pregnancies, in particular, are often difficult to differentiate from other pregnancy complications, due to the vagueness of the disease and the multiple ways the disease presents in patients.

As used herein "vascular disease or condition" refers to a disease or condition that results in abnormal circulation of blood. Vascular disease or condition includes atherosclerosis, a common disorder of the arteries caused by build-up of fats and other substances on artery walls, e.g. plaques. Plaques can rupture and lead to heart attack or stroke, also included in vascular diseases or conditions. Clots sometime form around plaques and interfere with blood flow or can also break off and damage the heart, lungs, or brain. Complications of atherosclerosis are also vascular diseases or conditions and include coronary artery disease, heart attack, transient ischemic attack or stroke, insufficient blood supply to the limbs, damage to organs, and atherosclerosis and obstruction of bypass grafts. Vascular disorders (vasculopathic conditions) also include arterial and venous thrombosis, thromboembolism, infarctions, vasospasm, angina, and unstable angina.

As used herein "platelet" is a blood component that recognizes and binds to a damaged area of a blood vessel, forming a clot. Platelets are usually obtained by taking a blood sample from an individual. In some embodiments, a platelet is isolated from a blood sample of an individual before determining the level of a complement component on the platelet.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F (ab)'$_2$, a dimer of Fab which itself is a light chain joined to $V_H$-$C_H$1 by a disulfide bond. The F (ab)'$_2$ may be reduced under mild conditions to break the disulfide linkage in the hinge region, thereby converting the F (ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many techniques known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current*

*Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* (3$^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

In one embodiment, the antibody is conjugated to an "effector" moiety. The effector moiety can be any number of molecules, including labeling moieties such as radioactive labels or fluorescent labels for use in diagnostic assays.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to a component of the complement pathway or to a marker of a white blood cell, polymorphic variants, alleles, orthologs, and conservatively modified variants, or splice variants, or portions thereof, can be selected to obtain only those polyclonal antibodies that are specifically immunoreactive with the component of the complement pathway or the marker of a white blood cell and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

An "antigen" is a molecule that is recognized and bound by an antibody, e.g., peptides, carbohydrates, organic molecules, or more complex molecules such as glycolipids and glycoproteins. The part of the antigen that is the target of antibody binding is an antigenic determinant and a small functional group that corresponds to a single antigenic determinant is called a hapten.

A "label" is a composition detectable by spectroscopic, photochemical, biochemical, immunochemical, or chemical means. For example, useful labels include $^{32}$P, $^{125}$I, fluorescent dyes, electron-dense reagents, enzymes (e.g., as commonly used in an ELISA), biotin, digoxigenin, or haptens and proteins for which antisera or monoclonal antibodies are available (e.g., antibody specific for a component of the complement pathway or a marker of a white blood cell can be made detectable, e.g., by incorporating a radiolabel or fluorescent label into the antibody, and used to detect component of the complement pathway or the marker of a white blood cell specifically reactive with the labeled antibody). A labeled secondary antibody can also be used to detect an antibody specific for a component of the complement pathway or a marker of a white blood cell.

The term "contact" or "contacting" is used herein interchangeably with the following: combined with, added to, mixed with, passed over, incubated with, flowed over, etc.

The term "immunoassay" is an assay that uses an antibody to specifically bind an antigen. The immunoassay is characterized by the use of specific binding properties of a particular antibody to isolate, target, and/or quantify the antigen.

In both instances, when speaking of "determination or determining" and "quantity," we mean to include both an amount or quantity of material. When more than one complement pathway component is measured, e.g., C4d and C3d "determination or determining" and "quantity," mean in addition, or alternatively, a ratio of a first complement pathway component to a second complement pathway component, e.g., a ratio of C4d to C3d.

Determination of the Level of a Complement Pathway Component on Erythrocytes or Platelets.

The invention involves conducting assays on blood components, e.g., erythrocytes or platelets, obtained from patients to determine levels of complement pathway components on the surface of the blood component. The levels of the complement pathway components are then compared to a control and used to diagnose or monitor an inflammatory disease or condition in an individual or to diagnose or monitor a vascular disease or condition in an individual. Cancers can also be monitored or diagnosed using the methods disclosed herein.

Samples of blood are obtained from the patient and are treated with EDTA (ethylenediaminetetraacetate) to inhibit complement activation. The samples are maintained at room temperature or under cold conditions. Assays are run preferably within 24 hours.

In some embodiments the erythrocytes are isolated from other components of the blood sample. For example, erythrocytes can be isolated from whole blood by centrifugation to remove other blood components. Platelets can be isolated from blood using an antibody specific for platelets, e.g., an anti-CD42b antibody. CD42b antibodies are commercially available, e.g., from BD Immunocytometry Systems, San Jose, Calif.

Isolation of platelets can be done by attaching an antibody or ligand specific to a platelet surface marker to a solid support, then contacting a sample containing platelets with the linked antibody. Contaminating cells are washed away allowing the isolated platelets to be collected. Erythrocytes can also be isolated using erythrocyte specific ligands or antibodies to a solid support.

In some embodiments, FACS is used to isolate an erythrocyte or platelet containing fraction of cells. The term "FACS" refers to fluorescence activated cell sorting, a technique used to separate cells according to their content of particular molecules of interest. The molecule of interest can be specific for a type of cell or for particular cell state. The molecule of interest can be fluorescently labeled directly by binding to a fluorescent dye, or by binding to a second molecule, which has been fluorescently labeled, e.g., an antibody, lectin or aptamer that has been fluorescently labeled and that specifically binds to the molecule of interest. Thus, erythrocyte or platelet specific markers can be used to isolate erythrocyte or platelet from other components of a blood sample. For erythrocytes, RNA content can by used to isolate erythrocytes from other cells in a blood sample, in particular, from immature red blood cells. In a preferred embodiment, RNA is detected by staining with a fluorescent dye, and reticulocytes are separated from mature red cells on the basis of fluorescence. Fluorescent dyes for staining RNA can include thiazole orange and auramine O.

Isolation of erythrocytes or platelets also refers to gating techniques used to assay a particular population of erythrocytes or platelets during flow cytometric analysis. A labeled marker specific for a population of interest is used to analyze the population. A second labeled marker is then used to determine the level of a complement pathway component on the population of interest, e.g., erythrocytes or platelets.

The determination of the level of a complement pathway component can be done by a number of methods including flow cytometry, ELISA using erythrocyte or platelet lysates, radioimmunoassay, and nephelometry. In one embodiment of this invention, the determination of the levels of a component of the complement pathway is made using flow cytometric methods, with measurements taken by direct or indirect immunofluorescence using polyclonal or monoclonal antibodies specific for the component of the complement pathway. The mean fluorescence channel (MFC) for the white blood cell component of the complement pathway is determined. Determination of complement components, e.g., C4d, CR1, and, on the surface of red blood cells or platelets is described in WO03/022223, published Mar. 20, 2003 and in U.S. Ser. No. 60/463,447, filed Apr. 16, 2003, both of which are herein incorporated by reference for all purposes.

In one embodiment, levels of a complement pathway component are determined on the surface of erythrocytes to diagnose or monitor the progression of an immune disease or condition in individuals or a subpopulation of individuals. The erythrocytes are isolated or detected using erythrocyte specific markers e.g., ligands, antibodies or nucleic acid biding dyes. Determination of complement pathway component levels can be done by a number of methods including flow cytometry, ELISA using erythrocyte lysates, and radioimmunoassay. In one embodiment of the invention, the determination of the levels of a complement pathway component is made using flow cytometric methods, with measurements taken by direct or indirect immunofluorescence using polyclonal or monoclonal antibodies specific for a complement pathway component. The mean fluorescence channel (MFC) for a complement pathway component is determined. The same type of assay may be used for diagnosis or for monitoring disease activity in patients known to have the immune disease or condition.

In another embodiment, levels of a complement pathway component are determined on the surface of platelets to diagnose or monitor the progression of a vascular disease or condition in individuals. The platelets are isolated or detected using platelet specific markers e.g., ligands, or antibodies such as anti-CD42b antibodies. Determination of complement pathway component levels can be done by a number of methods including flow cytometry, ELISA using platelet lysates, radioimmunoassay, and nephelometry. In one embodiment of the invention, the determination of the levels of a complement pathway component on a platelet is made using flow cytometric methods, with measurements taken by direct or indirect immunofluorescence using polyclonal or monoclonal antibodies specific for a complement pathway component. The mean fluorescence channel (MFC) for a complement pathway component is determined. The same type of assay may be used for diagnosis or for monitoring disease activity in patients known to have the vascular disease or condition. Nephelometry techniques can also be used for the determination.

Diagnostic Methods

In one embodiment, a subset of hepatitis C patients can be identified by determining the level of a complement pathway component on erythrocytes. For example, some hepatitis C patients have elevated levels of complement ligand Bb and/or complement ligand C3d on erythrocytes. The methods described above can be used e.g., to identify subsets of hepatitis C patients with cryoglobulinemia or other hepatitis C complications or to identify patients with hepatitis C that will respond to a particular therapeutic agent for treatment.

Figure 3:
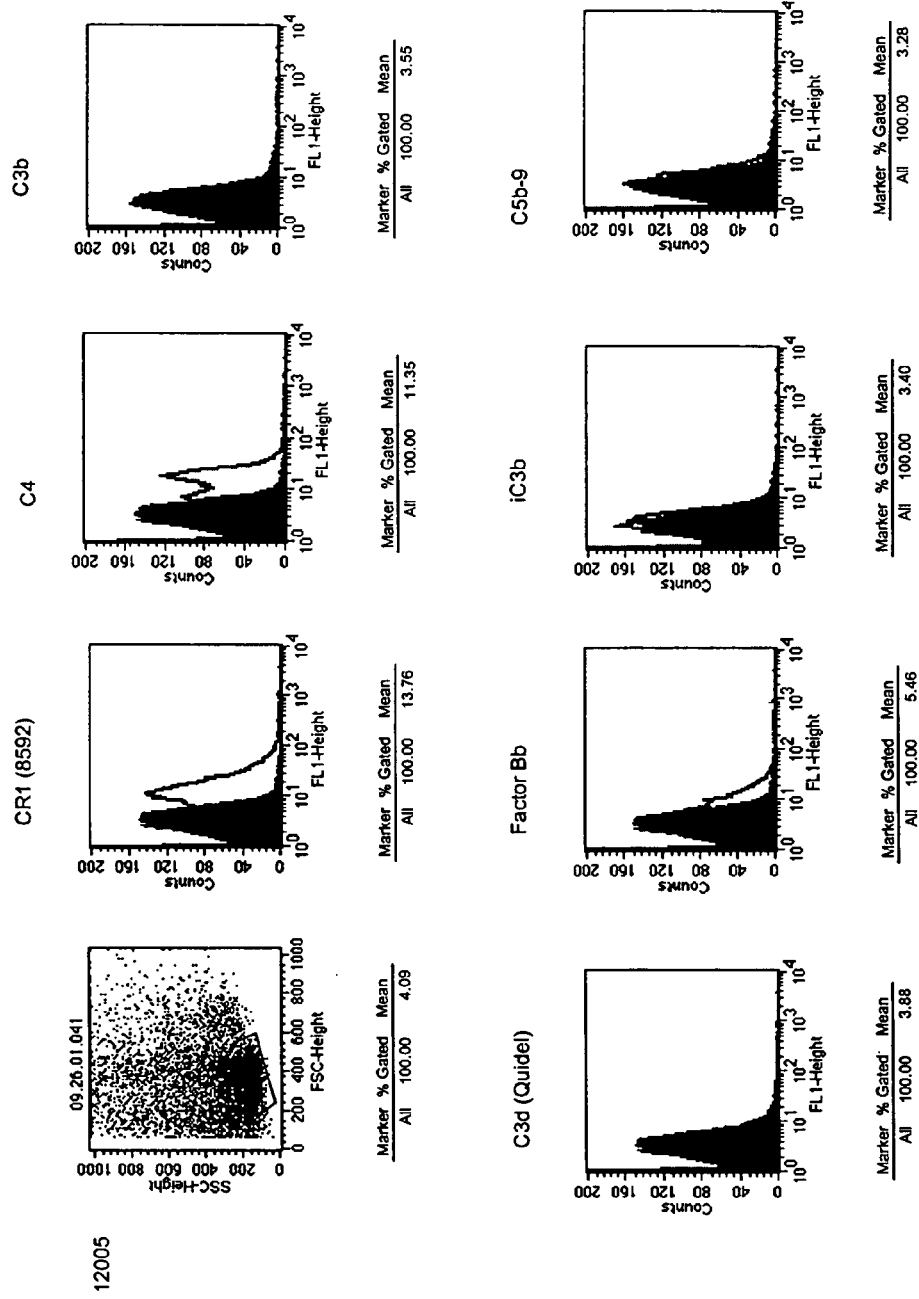
FIG. 3 provides a complement pathway component profile of erythrocytes from a second individual with sickle cell anemia.

In another embodiment, a subset of sickle cell anemia patients can be identified by determining the level of a complement pathway component on erythrocytes. For example, some sickle cell patients have abnormally low or undetectable levels of complement component C4d on erythrocytes. Other sickle cell patients have a population of erythrocytes with differing levels of complement component C4d (see e.g., FIG. 3). The methods described above can be used e.g., to identify subsets of sickle cell patients with vasoocclusive crisis or other sickle cell complications or to identify patients with sickle cell anemia that will respond to a particular therapeutic agent for treatment.

In another embodiment, a subset of patients with transplant complications can be identified by determining the level of a complement pathway component on erythrocytes. For example, some transplant patients have increased levels of complement component C4d and/or complement component C3d, and/or complement component iC3b on erythrocytes (see e.g., FIG. 5). The methods described above can be used e.g., to identify subsets of transplant patients with infections, or suffering from rejection or other transplant complications, or to identify transplant patients that will respond to a particular therapeutic agent for treatment.

In another embodiment, a subset of patients with pregnancy complications can be identified by determining the level of a complement pathway component on erythrocytes. For example, some pregnant patients have increased levels of complement component C4d and/or decreased levels of complement component CR1 on erythrocytes (see e.g., FIG. 6). The methods described above can be used e.g., to identify subsets of pregnant patients with preeclampsia, or other complications of pregnancy, or to identify pregnant patients that will respond to a particular therapeutic agent for treatment. The methods can be used to identify pregnancy complications such as preeclampsia in patients with SLE and patients that do not have SLE.

In another embodiment, a vascular disease, such as atherosclerosis is diagnosed or monitored by determining the level of a complement pathway component on platelets. For example, some SLE patients have increased levels of complement component C4-derived ligands on platelets. The methods described above can be used e.g., to diagnose or monitor vascular diseases in patients with SLE and patients that do not have SLE. The methods can also be used to identify subsets of patients with particular vascular diseases or to identify patients with a vascular disease or condition that will respond to a particular therapeutic agent for treatment. Methods of determining the level of a complement pathway component on platelets can also be used to identify patients at risk for infarctions, including e.g., myocardial infarctions, cerebral infarctions, ect.

Cancers can also be monitored or diagnosed using the methods disclosed herein.

Kits

Kits for conducting the assays for both the diagnosing or monitoring an inflammatory disease or condition are a part of this invention, as are kits for diagnosing or monitoring a vascular disease or condition. Said kits will use any of the various reagents needed to perform the methods described herein. For example using the immunofluorescence assays, the kits will generally comprise a conjugate of a monoclonal or polyclonal antibody specific for complement pathway component (e.g., anti-C4d or C3d antibodies) with a fluorescent moiety, and preferably also a conjugate of a monoclonal or polyclonal antibody specific for an erythrocyte or platelet (e.g., platelets using, e.g., anti-CD42b antibodies) with a different fluorescent moiety. The kit can also include a control level of complement pathway component or a means to determine such a control level. Additionally, the kits can comprise instructional material for the user and such other material as may be needed in carrying out assays of this type, for example, buffers, radiolabelled antibodies, colorimeter reagents etc.

The antibodies for use in these methods and kits are known. Antibodies specific for CD42b are available from Becton Dickinson Immunocytometry Systems, San Jose, Calif. Hybridomas secreting Anti-CR1 antibodies are available from the American Type Culture Collection in Maryland (ATCC #HB 8592). A general reference is U.S. Pat. No. 4,672,044. Anti-C4d, anti-C3d antibodies, anti-Bb antibodies, and anti-iC3b antibody are available from Quidel Corp. in San Diego, Calif. and are generally described in Rogers, J., N. Cooper, et al. *PNAS* 89:10016-10020, (1992); Schwab, C. et al., *Brain. Res.* 707(2):196 (1996); Gemmell, C. *J. Biomed. Mater. Res.* 37:474-480, (1997); and, Stoltzner, S. E., et al. *Am. J Path.* 156:489-499, (2000).

Automation and Computer Software

The determinations of complement pathway components e.g., C4d, C3d, Bb, CR1, and iC3b, and the diagnostic and disease activity monitoring methods described above can be carried out manually, but often are conveniently carried out using an automated system and/or equipment, in which the blood sample is analyzed automatically to make the necessary determination or determinations, and the comparison with the base or reference value is carried out automatically, using computer software appropriate to that purpose.

Thus, in one aspect, the invention comprises a method for diagnosing or monitoring an inflammatory disease or condition in an individual comprising (a) automatically determining, in a blood sample from the individual containing an erythrocyte or a platelet, complement pathway components deposited on surfaces of erythrocytes or platelets in the sample, and (b) automatically comparing said determinations with reference values for the same complement pathway components on surfaces of erythrocytes or platelets.

Computer software, or computer-readable media for use in the methods of this invention include:

(1): a computer readable medium, comprising:
code for receiving data corresponding to a determination of complement pathway components deposited on surfaces of erythrocytes or platelets;
code for retrieving a reference value for the same complement pathway components deposited on surfaces of erythrocytes or platelets of individuals; and
code for comparing the data in (a) with the reference value of (b).

In embodiments of the invention, one or more reference values may be stored in a memory associated with a digital computer. After data corresponding to a determination of the level of a complement pathway component is obtained (e.g., from an appropriate analytical instrument), the digital computer may compare the complement pathway component data with one or more appropriate reference values. After this comparison takes place, the digital computer can automatically determine if the data corresponding to the determination of complement pathway component is associated with an inflammatory disease or condition, or a vascular disease or condition.

Those of skill will recognize that computer programs can be modified to analyze levels of more than one complement pathway component on erythrocytes or platelets for diagnosis or monitoring an inflammatory disease or condition, or a vascular disease or condition.

Accordingly, some embodiments of the invention may be embodied by computer code that is executed by a digital computer. The digital computer may be a micro, mini or large frame computer using any standard or specialized operating system such as a Windows™ based operating system. The code may be stored on any suitable computer readable media. Examples of computer readable media include magnetic, electronic, or optical disks, tapes, sticks, chips, etc. The code may also be written by those of ordinary skill in the art and in any suitable computer programming language including, C, C++, etc.

EXAMPLES

The following examples are provided by way of illustration only and not by way of limitation. Those of skill will readily recognize a variety of noncritical parameters that could be changed or modified to yield essentially similar results.

Example 1

Diagnosis and Monitoring Hepatitis C Virus Infection Using Complement Pathway Components Red blood cells were pelleted, washed with PBSB, and aliquotted for anti-complement component or control antibody staining. Two-color flow cytometric analyses was performed to measure a series of complement components on erythrocytes of patients, e.g., CR1, C4d, C3b, C3d, Bb, iC3b, and C5b-9. Monoclonal antibodies (mAb) were added to red blood cells at a concentration of 10 µg/ml. An RNA binding dye was added to distinguish reticulocytes from erythrocytes. The cells were incubated for 20 min at 4° C., and washed with cold PBSB+0.2% sodium azide. A secondary antibody, goat anti-mouse IgG conjugated to fluorescein isothyocyanate (FITC) from Jackson Immunoresearch Laboratories (#115-096-062) was added to cells at a concentration of 10 µg/ml. Cells were incubated and washed, resuspended in PBSB+0.2% sodium azide, and analyzed by flow cytometry using a FACSCalibur (Becton Dickinson Immunocytometry Systems, San Jose, Calif.). Erythrocytes were gated for further analysis. Nonspecific binding of immunoglobulins to cells was determined by performing identical assays in parallel using the isotype control antibody MOPC21 (obtained from ATCC). A subset of patients with hepatitis C virus infection had significant levels of complement ligand Bb (E-Bb) and/or complement ligand C3d (E-C3d) on the surfaces of their erythrocytes were found (FIG. 1). In contrast to patients with SLE, patients with hepatitis C virus infection have normal levels of E-CR1 and E-C4d. Among patients infected with hepatitis C virus, a subset will develop autoimmune complications of the disease, some will have a disease course complicated by cryoglobulinemia, and some will respond to a specific therapy while others will not. Measurements of complement pathway components on erythrocytes (including but not limited to Bb and C3d) are used to identify such subsets of patients, leading to more effective and targeted therapeutic intervention.

Example 2

Diagnosis and Monitoring Sickle Cell Anemia Using Complement Pathway Components

Figure 2:
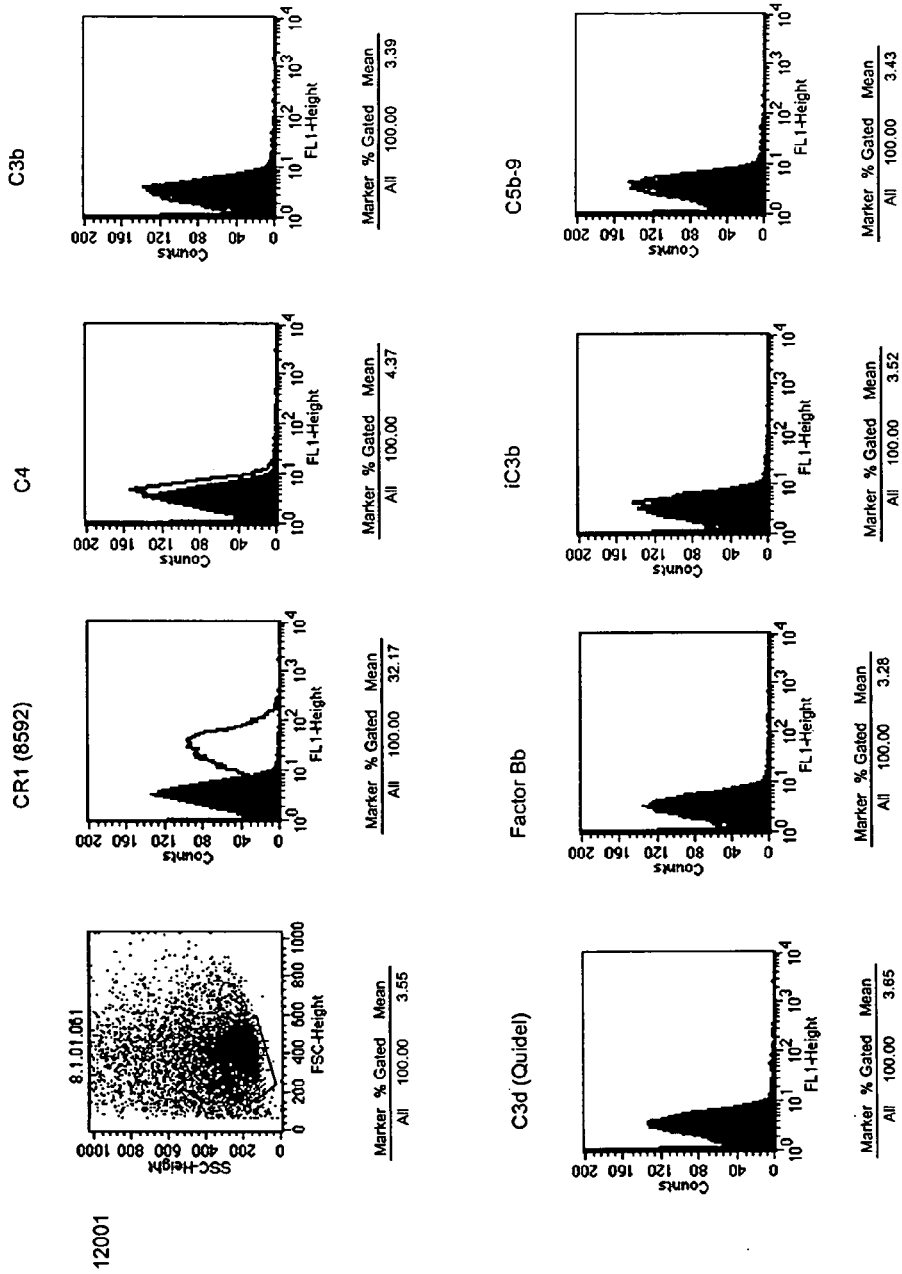
FIG. 2 provides a complement pathway component profile of erythrocytes from an individual with sickle cell anemia.

Complement pathway components were measured on erythrocytes from patients with sickle cell anemia as described above. A subset of patients with sickle cell anemia had abnormally low and/or undetectable levels of complement ligand C4d on the surfaces of their erythrocytes was discovered. See, e.g., FIG. 2. One patient with sickle cell anemia had two populations of erythrocytes that differ significantly in levels of E-C4d. See, e.g., FIG. 3. In contrast to patients with SLE, the observed population of patients with sickle cell anemia had normal levels of CR1. A subset of patients with sickle cell anemia have significantly more vasoocclusive crises. Measurements of complement ligands, including C4d, and receptors on erythrocytes is used to identify such subsets of patients, leading to more effective and targeted therapeutic intervention.

Example 3

Figure 4:
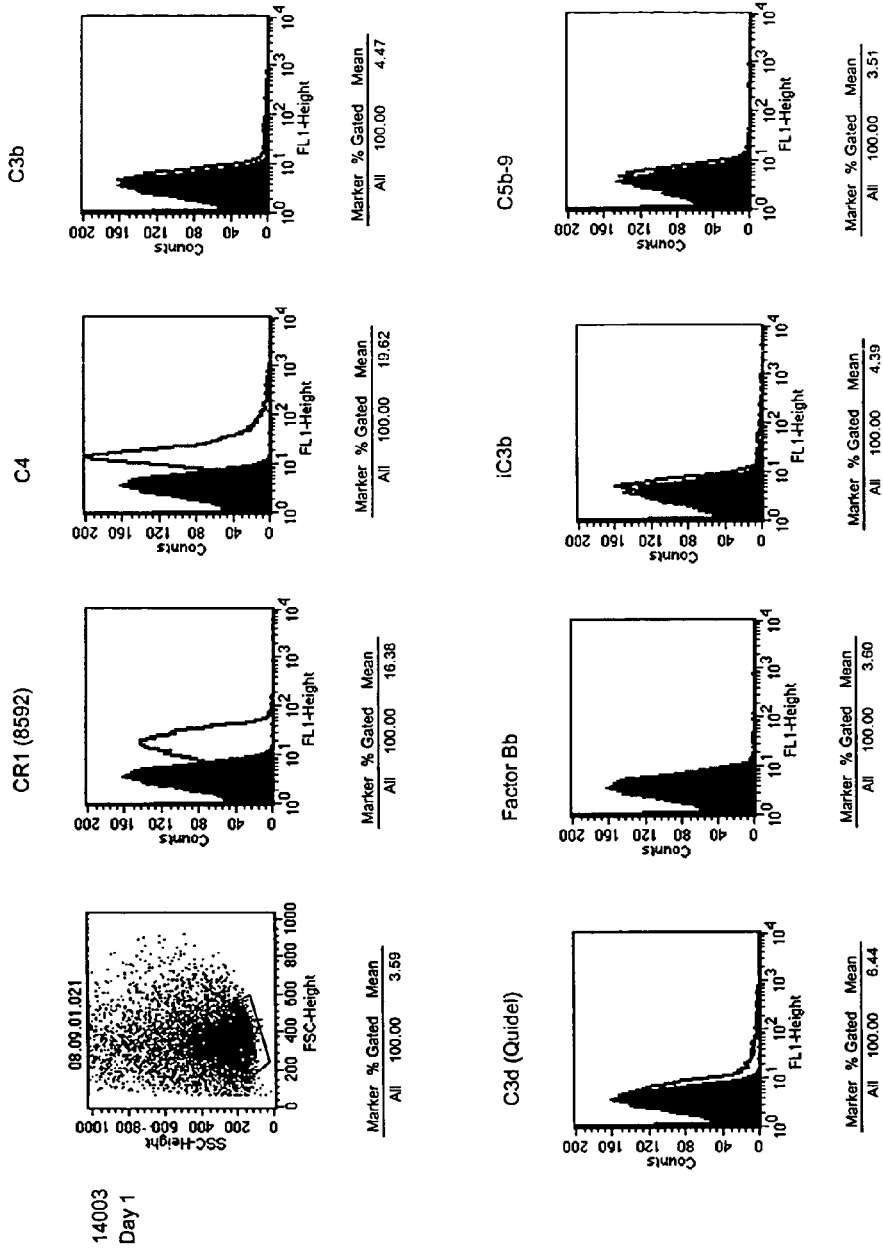
FIG. 4 provides a complement pathway component profile of erythrocytes from an individual before a stem cell transplant.
Figure 5:
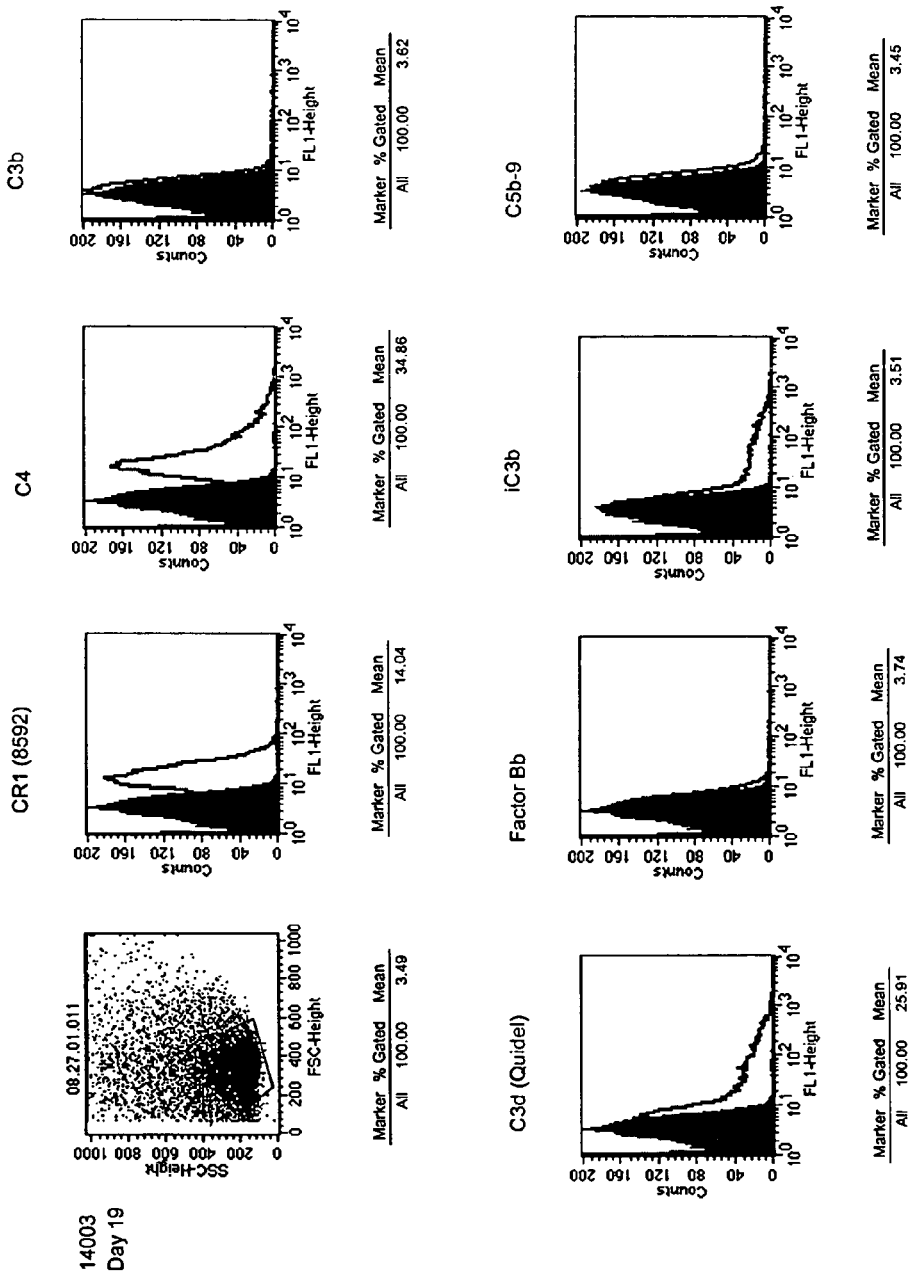
FIG. 5 provides a complement pathway component profile of erythrocytes from the individual shown in FIG. 4, after a stem cell transplant.

Diagnosis and Monitoring Transplant Complications Using Complement Pathway Components Complement pathway components were measured on erythrocytes from a patient before and after undergoing a stem cell transplant for hematologic malignancy using techniques described above. FIG. 4 provides a complement pathway component profile of a patient before receiving a stem cell transplant. After transplant the patient suffered complications. FIG. 5 provides the complement pathway component profile of the same patient nineteen days after receiving the transplant, while suffering from post-transplant complications, and demonstrates that the patient had abnormal levels of complement ligands C4d (increased), C3d (increased), and iC3b (increased) deposited on erythrocytes in the post-transplant period. In contrast to patients with SLE, transplant patients maintain normal levels of E-CR1. This suggests that circulating erythrocytes reflect early stages of transplant rejection, concurrent infection, or other complications of transplantation, through changes in levels of complement ligands and/or receptors on the erythrocyte surface. Measurements of complement ligands and receptors on erythrocytes are used to identify post-transplant complications, leading to more effective and targeted therapeutic intervention.

Example 4

Figure 6:
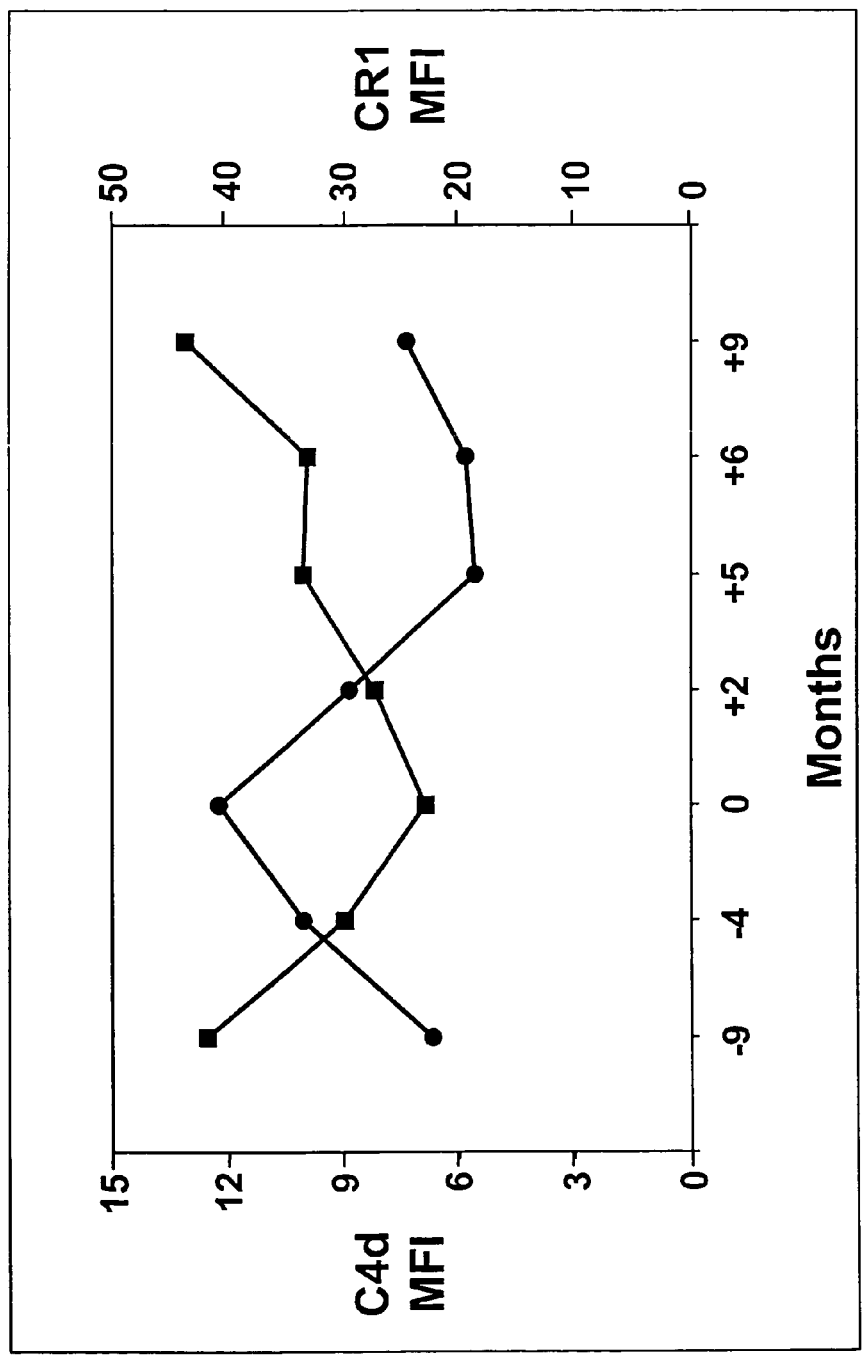
FIG. 6 provides levels of C4d and CR1 on erythrocytes of a pregnant individual before and after giving birth (month 0).

Diagnosis and Monitoring Complications of Pregnancy Using Complement Pathway Components Measurement of complement pathway components on surfaces of erythrocytes can facilitate diagnosis of complications of pregnancy such as preeclampsia and aid in the differentiation of disease flares in lupus pregnancy vs. complications of pregnancy. FIG. 6 shows a complement pathway component profiles on erythrocytes of a pregnant individual before giving birth and 9 months after. Complement pathway component levels were assayed as described above. In the figure, C4d levels are shown as circles and CR1 levels are shown as squares. During pregnancy levels of CR1 began to decrease soon after conception (−9 months), reaching a nadir at delivery (0 months) and gradually increased during the post-partum period, returning to normal 9 months after delivery. In addition, during pregnancy levels of C4d began to increase soon after conception (−9 months), reaching a peak at delivery (0 months) and gradually decreased during the post-partum period, returning to normal 9 months after delivery. These results mimic C4d and CR1 levels in SLE, but are much less pronounced. Thus, analysis of complement pathway component levels during pregnancy can be used to diagnose and monitor pregnancy complications and to distinguish those complications from lupus or lupus flares, particularly in patients with SLE.

Recent studies by others have demonstrated that fetal loss during pregnancy such as that observed in anti-phospholipid syndrome, is dependent on complement activation. Therefore, measurement of complement ligand and receptor levels on surfaces of erythrocytes can facilitate monitoring and prediction of outcomes of pregnancy.

Example 5

Diagnosis and Monitoring Vascular Diseases and Conditions Using Complement Pathway Components Atherosclerosis is an inflammatory disorder and numerous reports have identified C-reactive protein and other inflammatory proteins as potential biomarkers and prognostic indicators of disease progression. Young women with SLE have a 50-fold increased risk of heart attacks and strokes compared with healthy controls. Some patients with SLE have complement deposited on platelets. Thus, complement deposition on platelets may reflect and contribute to atherosclerosis and its complications, both in patients with SLE and in individuals that do not have SLE. Complement ligands on the surface of platelets were analyzed by flow cytometry and confocal microscopy in three experimental groups: 141 patients with SLE, 116 patients with other diseases, (including other autoimmune diseases, viral infections, and malignancies) and 101 healthy controls. Complement protein C4-derived ligands were detected on platelets from 27% of SLE patients, 2% of patients with other diseases, and 0% of healthy controls ($p=0.0001$). In addition, the presence of C4-derived fragments on platelets from patients with SLE was significantly correlated with history of a neurologic event ($p=0.006$) and antiphospholipid antibodies ($p=0.05$). Complement deposition could not be explained by concomitant deposition of immunoglobulin or by the presence of immune thrombocytopenic purpura (ITP). Patterns of complement deposition on platelet surfaces were captured by confocal microscopy and suggest diffuse rather than focal changes on the platelet membranes. These data support the following conclusions. First, although C4-derived ligands are present on normal erythrocytes, they are absent from normal platelet surfaces. Second, C4-positive platelets appear to be highly specific and diagnostic for patients with SLE. Third, identification of C4-positive platelets in patients with SLE is correlated with cardiovascular disease and vascular events. Fourth, identification of C4-positive platelets in patients with other diseases may identify patients at risk for cardiovascular disease and vascular events.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for monitoring an inflammatory disease or condition in an individual, wherein said inflammatory disease or condition is organ transplant rejection, the method comprising:
   (a) selecting an individual with an organ transplant;
   (b) determining a level of a complement pathway component C4d on an erythrocyte from the individual;
   (c) comparing the complement pathway component C4d level with a control level of complement pathway component C4d; and
   wherein an elevated C4d level from the control level of the complement pathway component C4d indicates that the individual has organ transplant rejection.

2. The method of claim 1, further comprising determining a level of at least one other complement pathway component on an erythrocyte.

3. The method of claim 2, wherein the one other complement pathway component is C3d.

4. The method of claim 1, wherein the level of complement pathway component C4d is determined using an antibody specific for complement component C4d.

5. The method of claim 4, wherein the antibody specific for complement pathway component C4d is labeled.

6. The method of claim 4, wherein the antibody specific for complement pathway component C4d is a monoclonal antibody.

7. The method of claim 1, further comprising
   (d) determining a level of a complement pathway component iC3b on an erythrocyte from the individual;
   (e) comparing the complement pathway component iC3b level with a control level of complement pathway component iC3b; and
   wherein an elevated iC3b level from the control level of the complement pathway component iC3b indicates that the individual has organ transplant rejection.

8. The method of claim 7, wherein the level of complement pathway component iC3b is determined using an antibody specific for complement component iC3b.

9. The method of claim 8, wherein the antibody specific for complement pathway component iC3b is labeled.

10. The method of claim 8, wherein the antibody specific for complement pathway component iC3b is a monoclonal antibody.

11. The method of claim 3, wherein the level of complement pathway component C3d is determined using an antibody specific for complement component C3d.

12. The method of claim 11, wherein the antibody specific for complement pathway component C3d is labeled.

13. The method of claim 11, wherein the antibody specific for complement pathway component C3d is a monoclonal antibody.

14. The method of claim 1, wherein the organ is a heart.

15. The method of claim 1, wherein the organ is a lung.

16. The method of claim 1, wherein the organ is a kidney.

* * * * *